(12) United States Patent
Kindler et al.

(10) Patent No.: US 6,297,407 B1
(45) Date of Patent: Oct. 2, 2001

(54) METHOD FOR PRODUCING ALKYNE DIOLS

(75) Inventors: Alois Kindler, Waldsee; Melanie Brunner, Schifferstadt; Christian Tragut, Wachenheim; Jochem Henkelmann, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/744,437

(22) PCT Filed: Aug. 13, 1999

(86) PCT No.: PCT/EP99/05933

§ 371 Date: Jan. 24, 2001

§ 102(e) Date: Jan. 24, 2001

(87) PCT Pub. No.: WO00/09465

PCT Pub. Date: Feb. 24, 2000

(30) Foreign Application Priority Data

Aug. 17, 1998  (DE) .............................................. 198 37 211

(51) Int. Cl.$^7$ .............................. C07C 31/18; C07C 33/04

(52) U.S. Cl. ............................. 568/855; 568/873; 568/874

(58) Field of Search ..................................... 568/855, 873, 568/874

(56) References Cited

FOREIGN PATENT DOCUMENTS

1354011-A * 5/1974 (GB) ............................. C07C/33/04

* cited by examiner

*Primary Examiner*—Samuel Barts
*Assistant Examiner*—Elvis O. Price
(74) *Attorney, Agent, or Firm*—Keil & Weinkauf

(57) ABSTRACT

The invention relates to a method for producing alkyne diols by reacting ketones with acetylenic hydrocarbons in an organic solvent in the presence of a base which contains potassium alcoholates of primary and/or secondary alcohols. The alkyne diols are produced while forming adducts which precipitate out of the reaction mixture and which are comprised of alkyne monoalcohols and/or alkyne diols and a base. The stoichiometries of the reaction partners are selected such that gelatinous adducts are formed which comprise a spherical surface, whereby the reaction mixture remains agitable during the entire reaction.

8 Claims, No Drawings

METHOD FOR PRODUCING ALKYNE DIOLS

This is the National phase Application of PCT/EP99/05933 Application filed Aug. 13, 1999.

This invention relates to a process for preparing alkynediols by reacting ketones with acetylenic hydrocarbons using potassium alkoxides.

A number of processes are known for preparing alkynediols.

Reppe's ethynylation process, reaction of aldehydes such as formaldehyde and acetaldehyde with acetylene over copper acetylide as catalyst, gives secondary alkynemonools and glycols in good yields. In the case of higher aldehydes, however, this method leads to unsatisfactory results.

The preparation of tertiary alkynediols by reacting ketones with acetylenic hydrocarbons using bases is particularly problematical. Most existing processes utilize finely divided, ideally water-free KOH powder in organic solvents such as THF, diisopropyl ether, dioxane, methylal or acetaldehyde dibutyl acetal. The disadvantage with these processes is that they mostly produce mixtures of monoalkynols and alkynediols containing an appreciable proportion of monoalkynols. A further disadvantage is that the suspensions formed in the solvents mentioned become so viscous through the formation of acicular crystalline adducts of KOH and tertiary monoalkynols and alkynediols that stirrability is appreciably compromised. As a result, efficient mixing and hence controlled dissipation of the heat of reaction is compromised or impossible. This leads to safety problems as well as low conversions. A possible use of larger solvent quantities has relatively small effect on the viscosity profile and is generally uneconomical, since the solvents used are costly.

EP-A 0 285 755 describes a process for preparing tertiary alkynediols by reacting ketones with acetylene. In particular, acetylene is reacted with carbonyl compounds and KOH powder as base. Alkyl tertbutyl ethers are used as solvents. The ketone and acetylene are used in a molar ratio of 1:1 to 3:1 and KOH and ketone in a molar ratio of 1:1 to 1.6:1. The solvent used is set to ensure efficiently stirrable reaction mixtures. However, it proved impossible to reproduce the teaching of this application (Comparative Example 2). Another disadvantage with this process is the use of specific, costly solvents, making the process uneconomical.

DE-A 20 08 675 describes the preparation of tertiary alkynediols by reacting ketones with acetylene using potassium alkoxides of primary and secondary alcohols of limited solubility in water. Aliphatic, cycloaliphatic and aromatic hydrocarbons can be used as solvents. Similarly, DE-A 20 47 446 describes the use of potassium alkoxides for preparing alkynediols by reacting alkynemonools with ketones.

In both processes, an increase in the viscosity of the reaction mixture in the course of the reaction is observed. Efficient mixing of the reaction batch and controlled dissipation of the heat of reaction are therefore compromised, so that the aforementioned problems arise in these processes, too.

It is an object of the present invention to provide a process for preparing alkynediols using an economically acceptable amount of a common organic solvent. The reaction mixture shall remain efficiently stirrable during the entire reaction time, ensuring controlled dissipation of the heat of reaction and good conversions.

We have found that this object is achieved by a process for preparing alkynediols by reacting ketones with acetylenic hydrocarbons in an organic solvent in the presence of a base comprising potassium alkoxides of primary and/or secondary alcohols to form adducts of alkynemonools and/or alkynediols and said base which precipitate from the reaction mixture by selecting the stoichiometries for the reaction partners so as to produce gellike adducts having a spherical surface, whereby the reaction mixture remains stirrable during the entire reaction.

The adducts which precipitate are adducts of the base with alkynmonools or alkynediols formed in the course of the reaction. Provided a certain stoichiometry is adhered to for the reaction partners, these adducts are gellike and not acicularly crystalline. A spherical surface for the purposes of the invention is a rounded, preferably spherelike surface of the kind present in gellike adducts. This ensures that there is none of the intermeshing which appreciably compromises stirrability as in the case of crystalline, acicular adducts and that instead the precipitated adducts are able to glide past one another when stirred. This permits the controlled dissipation of the heat of reaction and distinctly better mixing of the reaction partners. As well as having an advantageous effect on the conversions of the reaction, controlled dissipation of the heat of reaction is also desirable for safety reasons. If controlled dissipation of the heat of reaction is not ensured, the decomposition temperature of the substances present in the reaction mixture may be exceeded locally and this may give rise to spontaneous decompositions.

Acetylenic hydrocarbons for the purposes of the present invention are acetylene and monoalkynols prepared from carbonyl compounds and acetylene.

In a preferred embodiment of the process of the invention, acetylene is used as acetylenic hydrocarbon. Owing to the efficient mixing, the stoichiometry for the starting materials can be chosen in such a way that acetylene is used stoichiometrically with regard to the ketone. By stoichiometrically is meant a ratio of ketone to acetylene within the range from 1.9:1 to 2.1:1, preferably a ratio of 2:1. The ratio of potassium alkoxide to ketone is within the range from 0.9:1 to 2.1:1, preferably within the range from 1:1 to 1.5:1, particularly preferably within the range from 1.1:1 to 1.3:1. The alkoxide-to-ketone ratio chosen is an essential factor to ensure reaction mixture stirrability, since, at the ratio chosen, the adducts formed are not acicular but gellike and have a spherical surface.

The concentration of the reaction partners in the reaction mixture may be specified in terms of the weight ratio between ketone and a suspension of solvent and base. The concentration at which the reaction mixture remains efficiently stirrable depends on the reaction conditions and in particular on the ketone, solvent and alkoxide used. In the case of a suspension of potassium isobutoxide in xylene and acetone, the weight ratio between ketone and the suspension is generally not less than 1:2.5, preferably within the range from 1:2.5 to 1:8, particularly preferably 1:6.5.

In a further embodiment, the acetylenic hydrocarbons used are alkynemonools. Alkynemonools can be prepared by reacting acetylene with carbonyl compounds according to literature methods.

The carbonyl compounds used can be aliphatic and aromatic aldehydes and ketones. Preference is given to the use of ketones, with aliphatic ketones being particularly preferred. These can be linear, branched or cyclic. Preference is given to using ketones having from 3 to 8 carbon atoms, particularly preferably having from 3 to 6 carbon atoms, with acetone, methyl isobutyl ketone and cyclohexanone being very particularly preferred.

Accordingly, the acetylenemonools used are particularly preferably methylbutynol, 3,5-methylhex-1-yn-3-ol and 3-cyclohexylprop-1-yn-3-ol.

The ratio of alkynemonool to ketone is within the range from 1:0.8 to 1:1.2, preferably 1:1. The ratio of potassium alkoxide to ketone is within the range from 1.5:1 to 2.2:1, preferably within the range from 1.9:1 to 2.1:1, particularly preferably 2:1. The molar ratios chosen ensure reaction mixture stirrability and thus good conversions and controlled dissipation of heat.

The ketones used for the reaction with acetylenic hydrocarbons can be aliphatic and aromatic ketones. The use of aliphatic ketones is preferred. These can be linear, branched or cyclic. Particular preference is given to using aliphatic ketones having from 3 to 8 carbon atoms, very particularly preferably having from 3 to 6 carbon atoms. Among these, acetone, methyl isobutyl ketone and cyclohexanone are preferred. The use of acetone is very particularly preferred.

Suitable solvents are in particular hydrocarbons and ethers. Preference is given to the use of aliphatic and/or aromatic hydrocarbons. Particular preference is given to hydrocarbons having a boiling range from 80 to 180° C. Very particular preference is given to aliphatic hydrocarbons such as gasoline mixtures, cycloaliphatic hydrocarbons such as cyclohexane or aromatic hydrocarbons such as benzene, toluene, xylene, cumene or p-isopropylbenzene. The use of xylene is very particularly preferred.

The potassium alkoxides used are potassium alkoxides of secondary and/or primary alcohols. Alkoxides of $C_3$–$C_8$ alcohols, which can be linear, branched or cyclic, are preferred.

For example, it is possible to use the alkoxides of primary alcohols such as n-butanol, isobutanol, n-pentanol, 2-ethyl-4-butanol, 2-methyl-1-butanol, 2,2-dimethyl-1-propanol, hexanol, 2-ethylhexanol and also the potassium alkoxides of secondary alcohols such as 2-butanol, 2-pentanol, 3-pentanol, 2-methyl-3-butanol and cyclohexanol. Particular preference is given to the use of potassium butoxides, especially potassium isobutoxide.

A process for obtaining the potassium alkoxides is described in DE-A 20 08 675. Aqueous potassium hydroxide solution (a 50% strength by weight aqueous KOH solution, for example) is refluxed with excess alcohol. The resulting two-phase azeotrope with water separates at the top of a fractionating column into a lower aqueous phase, which is removed, and the alcohol which returns to the column as reflux. This quickly provides a solution of the desired potassium alkoxide. A hydrocarbon or ether having a higher boiling point than the alcohol used is added, and the excess alcohol is distilled off. What remains is an alcohol-free potassium alkoxide, partly suspended in the hydrocarbon, partly dissolved.

The reaction of acetylenic hydrocarbons with carbonyl compounds is preferably carried out using alcohol-free potassium alkoxides. However, the presence of alcohol is generally not a problem.

The base used is a mixture of KOH and potassium alkoxide or pure potassium alkoxide. For example, the weight ratio of KOH to potassium butoxide is preferably within the range from 30:70 to 0:100% by weight, particularly preferably within the range from 5:95 to 1:99% by weight. Very particular preference is given to a KOH-to-potassium butoxide ratio of 1:99% by weight.

The reaction temperature is generally within the range from 0 to 50° C., preferably within the range from 20 to 30° C. It is particularly preferable to conduct the reaction at about 30° C.

In a preferred embodiment, the first step is to prepare a suspension of potassium base and solvent. This is followed by the ketone and acetylene, or the ketone and the alkynemonool, being synchronously introduced in the appropriate molar ratio into the suspension of potassium base and solvent. The resulting reaction mixtures are efficiently stirrable in customary stirred tanks. The reaction time depends inter alia on the amount of starting materials used. It is for example within the range from 4 to 8 hours, preferably 6 hours, when 1 mol of base is used. The ketone and the acetylene or the alkynemonool are preferably added synchronously in the course of 4 hours and subsequently stirred together for 2 hours. After the reaction has ended, the batch is hydrolyzed with water, and most of the base passes into the aqueous phase as KOH. The resulting KOH solution can be removed by phase separation. The useful materials remain in the organic phase and, after hydrolysis and subsequent neutralization (preferably with glacial acetic acid), can be isolated by distillation. The solvent which is removed in the course of the distillation can be reused.

In the process of the invention, the reaction mixture is efficiently stirrable during the entire reaction. High yields of generally not less than 70%, preferably not less than 80%, are obtained as a result.

The Examples which follow illustrate the invention.

EXAMPLES

Inventive Example 1
Preparation of Dimethylhexynediol

A jacketed reactor equipped with a stirrer is charged with 114 g of xylene and 112 g of potassium isobutoxide (1 mol) [c(base)=5 mol/l]. The suspension is heated to 30° C. and maintained at that temperature during the reaction. 58 g of acetone (1 mol) and 13 g of acetylene (0.5 mol) are passed in concurrently over 4 hours. Following a post-reaction period of 2 h, the batch is hydrolyzed with 120 g of water. Following removal of the organic phase and neutralization with 7 g of glacial acetic acid, 61.5 g of dimethylhexynediol (corresponding to an 86% yield) are isolated from a conversion of 98% (based on acetone). In addition, the alkynemonool methylbutynol is obtained in a 4% yield.

Comparative Example 1

A jacketed reactor equipped with a stirrer is charged with 376 g of xylene and 97 g of potassium isobutoxide (0.87 mol) [c(base)=1.8 mol/l]. The suspension is heated to 30° C. and maintained at that temperature during the reaction. 92 g of acetone (1.59 mol) and 20 g of acetylene (0.77 mol) are passed in concurrently over 4 hours. Following a post-reaction period of 2 h, the batch is hydrolyzed with 105 g of water. Following removal of the organic phase and neutralization with 0.7 g of glacial acetic acid, 58.7 g of dimethylhexynediol (corresponding to a 52% yield) are isolated from a conversion of 86% (based on acetone). In addition, the alkynemonool methylbutynol is obtained in a 14.4% yield.

Comparative Example 2
(EP-A 0 285 755)

A jacketed reactor equipped with a stirrer is charged with 350 g of methyl tert-butyl ether and 74 g of potassium hydroxide powder (85%). The suspension is heated to 20° C. and maintained at that temperature during the reaction. 69.9 g of acetone and 15.6 g of acetylene are passed in concurrently over 4 hours. Following a post-reaction period of 1 h, the batch is hydrolyzed with 150 g of water. Following removal of the organic phase and neutralization with 13 g of glacial acetic acid, 61.3 g of dimethylhexynediol (corresponding to a 72% yield) are isolated from a conversion of 92% (based on acetone). The reaction batch became unstirrably solid toward the end of the reaction.

Inventive Example 2
Preparation of Dimethylhexynediol via Methylbutynol

A jacketed reactor equipped with a stirrer is charged with 114 g of xylene and 112 g of potassium isobutoxide (1 mol). The suspension is heated to 30° C. and maintained at that temperature during the reaction. 29 g of acetone (0.5 mol) and 42 g of methylbutynol (0.5 mol) are passed in concurrently over 4 hours. Following a post-reaction period of 2 h, the batch is hydrolyzed with 120 g of water. Following removal of the organic phase and neutralization with 13 g of glacial acetic acid, 58.7 g of dimethylhexynediol (corresponding to an 83% yield) are isolated from a conversion of 98% (based on acetone).

Comparative Example 3

A jacketed reactor equipped with a stirrer is charged with 114 g of xylene and 112 g of potassium isobutoxide (1 mol). The suspension is heated to 30° C. and maintained at that temperature during the reaction. 55.1 g of acetone (0.95 mol) and 80 g of methylbutynol (0.95 mol) are passed in concurrently over 4 hours. Following a post-reaction period of 2 h, the batch is hydrolyzed with 120 g of water. Following removal of the organic phase and neutralization with 21 g of glacial acetic acid, 93 g of dimethylhexynediol (corresponding to a 69% yield) are isolated from a conversion of 93% (based on acetone). In addition, the alkynemonool methylbutynol is obtained in a 14.3% yield.

Inventive Example 3
Preparation of 4,7-dihydroxy-2,4,7,9-tetramethylhex-5-yne

A jacketed reactor equipped with a stirrer is charged with 310 g of xylene and 224 g of potassium isobutoxide (2 mol). The suspension is heated to 30° C. and maintained at that temperature during the reaction. 200 g of methyl isobutyl ketone (2 mol) and 26 g of acetylene (1 mol) are passed in concurrently over 4 hours. Following a post-reaction period of 2 h, the batch is hydrolyzed with 230 g of water. Following removal of the organic phase and neutralization with glacial acetic acid, 330 g of 4,7-dihydroxy-2,4,7,9-tetramethylhex-5-yne (corresponding to a 73% yield) are isolated from a conversion of 89% (based on acetone).

Concentration dependence of selectivity of reaction of acetone with acetylene to form dimethylhexynediol using a suspension of potassium isobutoxide in xylene at various weight ratios between the potassium base in xylene and acetone Inventive Example 4
Preparation of Dimethylhexynediol (Potassium Base in Xylene/acetone=6.4)

A jacketed reactor equipped with a stirrer is charged with 228 g of xylene and 112 g of potassium isobutoxide. The suspension is heated to 30° C. and maintained at that temperature during the reaction. 53.3 g of acetone and 11.7 g of acetylene are passed in concurrently over 4 hours. Following a post-reaction period of 2 h, the batch is hydrolyzed with 120 g of water. Following removal of the organic phase and neutralization with 13 g of glacial acetic acid, 57.1 g of dimethylhexynediol (corresponding to an 88% yield) are isolated from a conversion of 98%. In addition, the alkynemonool methylbutynol is obtained in a 7% yield.

Inventive Example 5
Preparation of Dimethylhexynediol (Potassium Base in Xylene/acetone=4.5)

A jacketed reactor equipped with a stirrer is charged with 114 g of xylene and 112 g of potassium isobutoxide. The suspension is heated to 30° C. and maintained at that temperature during the reaction. 53.3 g of acetone and 11.7 g of acetylene are passed in concurrently over 4 hours. Following a post-reaction period of 2 h, the batch is hydrolyzed with 120 g of water. Following removal of the organic phase and neutralization with 11 g of glacial acetic acid, 56.7 g of dimethylhexynediol (corresponding to an 87% yield) are isolated from a conversion of 98%. In addition, the alkynemonool methylbutynol is obtained in a 7% yield.

Inventive Example 6
Preparation of Dimethylhexynediol (Potassium Base in Xylene/acetone=3.6)

A jacketed reactor equipped with a stirrer is charged with 80 g of xylene and 112 g of potassium isobutoxide. The suspension is heated to 30° C. and maintained at that temperature during the reaction. 53.5 g of acetone and 11.7 g of acetylene are passed in concurrently over 4 hours. Following a post-reaction period of 2 h, the batch is hydrolyzed with 120 g of water. Following removal of the organic phase and neutralization with 15 g of glacial acetic acid, 51.8 g of dimethylhexynediol (corresponding to a 79% yield) are isolated from a conversion of 98%. In addition, the alkynemonool methylbutynol is obtained in a 5% yield.

Inventive Example 7
Preparation of Dimethylhexynediol (Potassium Base in Xylene/acetone=3.2)

A jacketed reactor equipped with a stirrer is charged with 114 g of xylene and 224 g of potassium isobutoxide. The suspension is heated to 30° C. and maintained at that temperature during the reaction. 107 g of acetone and 23.4 g of acetylene are passed in concurrently over 4 hours. Following a post-reaction period of 2 h, the batch is hydrolyzed with 240 g of water. Following removal of the organic phase and neutralization with 18 g of glacial acetic acid, 91.6 g of dimethylhexynediol (corresponding to a 70% yield) are isolated from a conversion of 98%. In addition, the alkynemonool methylbutynol is obtained in a 4% yield.

We claim:

1. In a process for preparing alkynediols by reacting ketones with acetylenic hydrocarbons selected from the group consisting of acetylene and alkynemonool in an organic solvent in the presence of a base comprising potassium alkoxides of primary and/or secondary alcohols to form adducts of alkynemonools and/or alkynediols and said base which precipitate from the reaction mixture, the improvement which comprises, using as acetylenic hydrocarbon acetylene in the ratio of ketone to acetylene from 1.9 to 2.1:1 and the ratio of potassium alkoxide to ketone is within the range from 0.9 to 2.1:1 and using as acetylenic hydrocarbon alkynemonool in the ratio of alkynemonool to ketone from 1:0.8 to 1.2 and the ratio of potassium alkoxide to ketone is within the range from 1.5 to 2.2:1, so as to produce gel like adducts having a spherical surface, whereby the reaction mixture remains stirrable during the entire reaction.

2. A process as claimed in claim 1, wherein, using as acetylenic hydrocarbon acetylene, it is used in a stoichiometric amount with regard to the ketone and ratio of potassium alkoxide to ketone is within the range from 1:1 to 1.5:1.

3. A process as claimed in claim 2, wherein the ratio of potassium alkoxide to ketone is within the range from 1.1:1 to 1.3:1.

4. A process as claimed in claim 1, wherein, using as acetylenic hydrocarbon alkynemonool the ratio of alkynemonool to ketone is within the range from 1:1 and the ratio of potassium alkoxide to ketone is within the range from 1.9:1 to 2.1:1.

5. a process as claimed in claim 1, wherein ketones selected from acetone, methyl isobutyl ketone and cyclohexanone are used.

6. A process as claimed in claim 5, wherein acetone is used as ketone.

7. A process as claimed in claim 1, wherein hydrocarbons are used as solvents.

8. A process as claimed in claim 1, wherein the potassium alkoxides used are potassium butoxides.

* * * * *

UNITED STATES PATENT AND TRADEMARK OFFICE
CERTIFICATE OF CORRECTION

PATENT NO. : 6,297,407 B1
DATED : October 2, 2001
INVENTOR(S) : Kindler et al.

It is certified that error appears in the above-identified patent and that said Letters Patent is hereby corrected as shown below:

<u>Column 7,</u>
Line 6, "a" should be -- A --.

Signed and Sealed this

Fourteenth Day of May, 2002

*Attest:*

*Attesting Officer*

JAMES E. ROGAN
*Director of the United States Patent and Trademark Office*